United States Patent [19]

Bethge et al.

[11] 4,411,840

[45] Oct. 25, 1983

[54] PROCESS FOR THE RESOLUTION OF THE RACEMATE S-(CARBOXYMETHYL)-(RS)-CYSTEINE (B)

[75] Inventors: Horst Bethge; Axel Kleemann, both of Hanau; Jürgen Martens, Alzenau, all of Fed. Rep. of Germany

[73] Assignee: Degussa Aktiengesellschaft, Frankfurt, Fed. Rep. of Germany

[21] Appl. No.: 411,326

[22] Filed: Aug. 25, 1982

[30] Foreign Application Priority Data

Aug. 28, 1981 [DE] Fed. Rep. of Germany ....... 3134106

[51] Int. Cl.$^3$ .............................................. C07C 99/12
[52] U.S. Cl. ................................ 260/501.12; 562/401
[58] Field of Search .................. 260/501.12; 562/401, 562/554; 564/374

[56] References Cited

U.S. PATENT DOCUMENTS 3,808,268  4/1974  Rambacher et al. ................. 562/401
4,224,457  9/1980  Iwao et al. ........................... 562/401
4,245,117  1/1981  Scherberich ......................... 562/554

FOREIGN PATENT DOCUMENTS 1795021  12/1971  Fed. Rep. of Germany ...... 562/554
2545748   4/1978  Fed. Rep. of Germany ...... 562/554
2653332   6/1978  Fed. Rep. of Germany ...... 562/554
2147812   4/1973  France ................................ 562/554

OTHER PUBLICATIONS

Vigneaud, J. Amer. Chem. Soc. Vol. 52, pp. 4500–4504 (1930) Armstrong, J. Org. Chem. Vol. 16, pp. 749–753 (1951) Org. Syntheses Vol. 5 (1925), pp. 39–41.

Primary Examiner—James H. Reamer
Attorney, Agent, or Firm—Cushman, Darby & Cushman

[57] ABSTRACT

There is described the resolution of the racemate S-(carboxymethyl)-(RS)-cysteine. It is carried out by means of the optical isomers of 1-phenyl-ethylamine. This process makes it possible to obtain in a simple manner S-(carboxymethyl)-(R)-cysteine which is important for pharmaceutical purposes and is made from synthetically produced cysteine.

13 Claims, No Drawings

PROCESS FOR THE RESOLUTION OF THE RACEMATE S-(CARBOXYMETHYL)-(RS)-CYSTEINE (B)

BACKGROUND OF THE INVENTION

The invention is directed to a process for the resolution of the racemate S-(carboxymethyl)-(RS)-cysteine, especially for the purpose of recovery of S-(carboxymethyl)-(R)-cysteine. This substance is needed for pharmaceutical purposes and serves for example, as a mucolyticum.

It is known to produce S-(carboxymethyl)-(R)-cysteine by reacting (R)-cysteine—also called L-cysteine—with chloroacetic acid in alkali medium (Armstrong, J. Org. Chem., Vol. 16 (1951), pages 749 to 753).

The (R)-cysteine needed for this purpose as starting material is generally obtained from keratin containing natural materials. For this purpose these are hydrolyzed; the (RR)-cystine set free is separated and reduced to (R)-cysteine (Org. Synth., Vol. 5 (1925), pages 39 to 41); German OS No. 2653332 (and related Scherberich U.S. Pat. No. 4,245,117), Vigneaud, J. Amer. Chem. Soc., Vol. 52 (1930), pages 4500–4504). However, suitable natural materials are only available to a limited extent.

In the synthetic production of cysteine, for example from thiazolines-3 substituted in the 2-position via the corresponding thiazolidin-4-carbonitrile the racemate (RS)-cysteine is formed (German OS No. 2645748). It is known to obtain (R)-cysteine by reacting the (RS)-cysteine with dicyanidiamide to form (RS)-2-guanidine-1,3-thiazolidin-4-carboxylic acid, from this with the help of the copper complex salt of (R)-aspartic acid there is separated the (R)-2-guanidin-1,3-thiazolidin-4-carboxylic acid and subsequently there is split off from this the (R)-cysteine (German AS No. 1795021). This process for the recovery of the (R)-cysteine thus is cumbersome and expensive which is unsuited for use on an industrial scale.

SUMMARY OF THE INVENTION

It has now been found that the racemate S-(carboxymethyl)-(RS)-cysteine is resolved by means of the optical isomers of 1-phenyl-ethylamine. While in the previous process first (R)-cysteine is obtained in a given case through the cumbersome resolution of the racemate (RS)-cysteine, and the (R)-cysteine reacted to S-(carboxymethyl)-(R)-cysteine, rather now there is first reacted (RS)-cysteine to S-(carboxymethyl)-(RS)-cysteine and then this racemate resolved. This resolution can be carried out in a simple manner and yields the optical isomers of the S-(carboxymethyl)-cysteine in high yields in outstanding optical and chemical purity.

The S-(carboxymethyl)-(RS)-cysteine is produced from the (RS)-cysteine in the same and known manner as S-(carboxymethyl)-(R)-cysteine from the (R)-cysteine, namely for example, by conversion by means of chloroacetic acid in alkaline medium according to the process set forth in Armstrong, J. Org. Chem., Vol. 16 (1951), pages 749–753.

According to the invention the S-(carboxymethyl)-(R)-cysteine is separated from the racemate by means of (R)-1-phenyl-ethylamine and the S-(carboxymethyl)-(S)-cysteine by means of (S)-1-phenyl-ethylamine. The salts formed from (R)-1-phenyl-ethylamine and S-(carboxymethyl)-(R)-cysteine as well as from (S)-1-phenyl-ethylamine and S-(carboxymethyl)-(S)-cysteine previously have not been described. The salt of (R)-1-phenyl-ethylamine and S-(carboxymethyl)-(R)-cysteine is considerably less soluble than the diastereomer salt thereto from (R)-1-phenyl-ethylamine and S-(carboxymethyl)-(S)-cysteine; the salt from (S)-1-phenyl-ethylamine and S-(carboxymethyl)-(S)-cysteine is considerably less soluble than the diastereomer salt thereto from (S)-1-phenyl-ethylamine and S-(carboxymethyl)-(R)-cysteine.

To carry out the process of the invention the procedure is as customary in the resolution of a racemate. The racemate S-(carboxymethyl)-(RS)-cysteine in the presence of a solvent is brought together with the desired optical isomer of 1-phenylethylamine, and then the diastereomer salts formed are separated.

The salts which are diastereomers to each other show sufficiently large differences in solubility in numerous solvents. For example water belongs to this class of solvents. Preferably there are used as solvents primary or secondary alkanols having up to 6 carbon atoms or ethers and among these solvents especially those which are unlimitedly miscible with water. For example, there can be used hexan-1-ol, butan-1-ol, methyl tert.butyl ether and especially methanol, ethanol, propan-2-ol, dioxane and tetrahydrofuran. Other solvents include propan-1-ol, butan-2-ol, 2-methyl-propan-1-ol. The solvents can also be used in mixtures with each other or in mixtures with water, but the mixtures are suitably so selected that the solvents form a single phase.

The racemate S-(carboxymethyl)-(RS)-cysteine can be employed in solid form or as a suspension or solution in the solvent, the optical isomer of the 1-phenyl-ethylamine either diluted with a solvent or undiluted. The optical isomer of 1-phenyl-ethylamine and the racemate S-(carboxymethyl)-(RS)-cysteine can be employed in any desired proportion to each other. However, generally it is suitable to employ per mole of the racemate not less than about 0.5 and not more than about 5.0 moles of the optical isomer. Preferably, per mole of the racemate there is used 0.8 to 1.1, especially 1.0 mole of the optical isomer. There can be employed all temperatures at which the solvent is present in liquid form.

For separation of the diastereomer salts the preferred procedure is by a fractional crystallization in the customary manner. The mixture is brought to elevated temperatures, preferably to temperatures near the boiling point, so much solvent used that all materials are dissolved, and subsequently the solution cooled for the crystallization.

The concerned S-(carboxymethyl)-cysteine enantiomer is separated from the precipitated salts from S-(carboxymethyl)-(R)-cysteine and (R)-1-phenyl-ethylamine or S-(carboxymethyl)-(S)-cysteine and (S)-1-phenylethylamine by treating the salts with strong acids, preferably strong mineral acids such as hydrochloric acid. Other mineral acids include hydrobromic acid and sulfuric acid.

Unless otherwise indicated all parts and percentages are by weight.

The compositions can comprise, consist essentially of, or consist of the stated materials and the process can comprise, consist essentially of, or consist of the stated materials.

DETAILED DESCRIPTION

Examples

The optically active materials obtained in each case were examined as to their specific rotation $[\alpha]_D^{20}$. This is given in degrees·cm$^3$/dm.g. Percent data are weight percents.

A. PRODUCTION OF S-(CARBOXYMETHYL)-(RS)-CYSTEINE

As starting material there served (RS)-cysteine hydrochloride which was produced by the process of German OS No. 2645748. 140 grams (1 mole) of this material together with 160 grams (4 moles) of sodium hydroxide were dissolved in 1000 ml of water. To this solution there was first added 3 grams of sodium hydrogen sulfide and then in the course of 45 minutes 95 grams (1 mole) of monochloroacetic acid. The temperature of the mixture in the meanwhile was held at 20° C. and after that held for 3 hours at 20° to 30° C. The reaction mixture was subsequently adjusted to a pH of 3.0 by addition of concentrated, aqueous hydrochloric acid. Hereby the S-(carboxymethyl)-(RS)-cysteine separated out. It was filtered off at 10° C. and washed with water until it was free from chloride ions. Then it was dried under reduced pressure at 105° C. The yield was 173 grams, corresponding to 97% based on the cysteine hydrochloride employed. The melting point (decomposition point) of the S-(carboxymethyl)-(RS)-cysteine was 188° to 192° C.

B. RESOLUTION OF THE RACEMATE S-(CARBOXYMETHYL)-(RS)-CYSTEINE

Example 1

100 grams (0.56 mole) of the racemate S-(carboxymethyl)-(RS)-cysteine obtained according to process A were suspended in 1500 ml of methanol. There were added to the suspension 50 ml of water and 1000 ml (0.78 mole) of (S)-1-phenyl-ethylamine. The mixture was held for one hour under reflux at the boiling point, then slowly cooled to 25° C. and filtered with suction. The residue was washed with 150 ml of methanol and dried at 30° C. and 25 mbar. The material recovered was the salt of S-(carboxymethyl)-(S)-cysteine and (S)-1-phenyl-ethylamine. The yield was 42.5 grams, corresponding to 50%, based on the S-(carboxymethyl)-(S)-cysteine contained in the racemate. The specific rotation of the salt obtained was +20.5° (c=1 in water). The elemental analysis showed C=51.81% (51.98%); H=6.69 (6.71%); N=9.58% (9.32%); S=10.79% (10.68%). (In parantheses calculated for $C_{13}H_{20}N_2O_4S$).

36.5 grams of the salt of S-(carboxymethyl)-(S)-cysteine and (S)-1-phenyl-ethylamine were dissolved in 100 ml of water. There were mixed into the solution 300 ml of methanol and the mixture adjusted to a pH of 3.0 with concentrated, aqueous hydrochloric acid. Hereby the S-(carboxymethyl)-(S)-cysteine precipitated. It was filtered off under suction, washed with 30 ml of cold water and dried at 105° C. and 25 mbar. The yield was 21.9 grams, corresponding to 100% based on the salt employed. The melting point (decomposition point) of the S-(carboxymethyl)-(S)-cysteine was 188° to 192° C. and the specific rotation +33.6° (c=10 in aqueous sodium hydroxide solution, pH 6.0).

EXAMPLE 2

The procedure was as in Example B1 but instead of (S)-1-phenyl-ethylamine there were employed 100 ml of (R)-1-phenyl-ethylamine.[*] The yield was 42.2 grams, corresponding to 50%. The rotation of the salt was −20.4° (c=1 in water). The elemental analysis was C=51.79% (51.98%); H=6.58% (6.71%); N=9.30% (9.32%); S=10.60% (10.68%). (In parantheses calculated for $C_{13}H_{20}N_2O_4S$.)

[*]There was obtained the salt of S-(carboxymethyl)-(R)-cysteine and (R)-1-phenyl-ethylamine.

From 36.5 grams of the salt of S-(carboxymethyl)-(R)-cysteine and (R)-1-phenyl-ethylamine there were obtained 21.9 grams, corresponding to 100% yield of S-(carboxymethyl)-(R)-cysteine. The melting point (decomposition point) was 187° to 190° C. and the rotation −33.6° (c=10 in aqueous sodium hydroxide solution, pH 6.0).

The entire disclosure of German priority application No. P 3134106.3 is hereby incorporated by reference.

What is claimed is:

1. A process of resolving the racemate S-(carboxymethyl)-(RS)-cysteine comprising dissolving the racemate together with an optical isomer of 1-phenyl-ethylamine in a solvent in which the salt of said optical isomer with one of the isomer present, said racemate is less soluble than the salt of said optical isomer with the other one of the isomers present in said racemate and precipitating the less soluble salt.

2. A process according to claim 1 wherein the solvent is water, a primary or secondary alkanol having 1 to 6 carbon atoms, an ether, or a mixture of such solvents.

3. A process according to claim 2 wherein the solvent is methanol, ethanol, propan-2-ol, dioxane or tetrahydrofuran, or a mixture of such solvent with a minor amount of water.

4. A process according to claim 3 wherein the solvent is anhydrous.

5. A process according to claim 3 wherein the solvent contains a minor amount of water.

6. A process according to claim 2 wherein the solvent comprises an alkanol having 1 to 6 carbon atoms.

7. A process according to claim 2 wherein the solvent comprises methyl tert.butyl ether, dioxane, or tetrahydrofuran.

8. A process according to claim 3 wherein the solvent comprises methanol, ethanol, or propan-2-ol.

9. A compound which is either (1) a salt of S-(carboxymethyl)-(R)-cysteine and (R)-1-phenylethylamine or (2) a salt of S-(carboxymethyl)-(S)-cysteine and (S)-1-phenyl-ethylamine.

10. A compound according to claim 9 which is a salt of S-(carboxymethyl)-(R)-cysteine and (R)-1-phenyl-ethylamine.

11. A composition comprising the compound of claim 10 substantially free from the salt of S-(carboxymethyl)-(S)-cysteine and (R)-1-phenyl-ethylamine.

12. A compound according to claim 9 which is a salt of S-(carboxymethyl)-(S)-cysteine and (S)-1-phenyl-ethylamine.

13. A composition comprising the compound of claim 12 substantially free from the salt of S-(carboxymethyl)-(R)-cysteine and (S)-1-phenyl-ethylamine.

* * * * *